US010231618B2

(12) United States Patent
Doble et al.

(10) Patent No.: US 10,231,618 B2
(45) Date of Patent: Mar. 19, 2019

(54) RAPID MEASUREMENT OF INDIVIDUAL CONE PHOTORECEPTOR POINTING FOR EVALUATION OF EYE HEALTH USING FOCUS DIVERSITY

(71) Applicants: OHIO STATE INNOVATION FOUNDATION, Columbus, OH (US); ARIZONA BOARD OF REGENTS ON BEHALF OF THE UNIVERSITY OF ARIZONA, Tucson, AZ (US)

(72) Inventors: Nathan Doble, Dublin, OH (US); Leonardo Blanco, Paris (FR); Johanan Codona, Tucson, AZ (US); Hugh Morris, Upper Arlington, OH (US)

(73) Assignees: OHIO STATE INNOVATION FOUNDATION, Columbus, OH (US); THE ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 0 days.

(21) Appl. No.: 15/570,328

(22) PCT Filed: Apr. 28, 2016

(86) PCT No.: PCT/US2016/029717
§ 371 (c)(1),
(2) Date: Oct. 28, 2017

(87) PCT Pub. No.: WO2016/176415
PCT Pub. Date: Nov. 3, 2016

(65) Prior Publication Data
US 2018/0125359 A1 May 10, 2018

Related U.S. Application Data

(60) Provisional application No. 62/154,490, filed on Apr. 29, 2015.

(51) Int. Cl.
*A61B 3/14* (2006.01)
*A61B 3/12* (2006.01)
(Continued)

(52) U.S. Cl.
CPC ............ *A61B 3/12* (2013.01); *A61B 3/0025* (2013.01); *A61B 3/102* (2013.01); *A61B 3/14* (2013.01);
(Continued)

(58) Field of Classification Search
CPC .......... A61B 3/0008; A61B 3/10; A61B 3/12; A61B 3/0075; A61B 3/102; A61B 3/1025; A61F 2009/00863; G01B 9/02091
(Continued)

(56) References Cited

U.S. PATENT DOCUMENTS 6,916,096 B2 7/2005 Eberl et al.
8,684,946 B1 4/2014 Sims et al.
(Continued)

OTHER PUBLICATIONS

Bedell et al., "Photoreceptor orientation. A graded disturbance bordering a region of choroidal atrophy," Arch Ophthalmol, 1981, 99(10)1841-1844.
(Continued)

*Primary Examiner* — Mahidere S Sahle
(74) *Attorney, Agent, or Firm* — Michael Best & Friedrich LLP (57) ABSTRACT

Systems and methods are described for measuring angular direction of individual photoreceptors in an eye. A light source is projected through the pupil of the eye onto the retina. An image of the light reflected back from the plurality of photoreceptors is captured at a first focal depth and then at a second focal depth, where the first focal depth is different than the second focal depth. At least one individual photoreceptor is identified in both images and a lateral
(Continued)

difference of the position of the identified photoreceptor is measured. The angular direction of the photoreceptor is then calculated based on the measured lateral difference.

19 Claims, 5 Drawing Sheets

(51) Int. Cl.
    *G06T 7/73*     (2017.01)
    *A61B 3/00*     (2006.01)
    *A61B 3/10*     (2006.01)
    *A61B 3/024*     (2006.01)

(52) U.S. Cl.
CPC ............... *G06T 7/74* (2017.01); *A61B 3/024* (2013.01); *A61B 3/1025* (2013.01); *G06T 2207/10101* (2013.01); *G06T 2207/20221* (2013.01); *G06T 2207/30041* (2013.01)

(58) Field of Classification Search
USPC .................................................. 351/206, 246
See application file for complete search history.

(56) References Cited

U.S. PATENT DOCUMENTS

2009/0231545 A1    9/2009    Peyman
2010/0290007 A1    11/2010    Van De Velde
2013/0128227 A1    5/2013    Cui et al.

OTHER PUBLICATIONS

Birch et al., "The Stiles-Crawford effect in retinitis pigmentosa," Invest Ophthalmol Vis Sci, 1982, 22(2):157-164.
Blanco et al., "Rapid Measurement of Cone Photoreceptor Pointing Using Focus Diversity," Conference Poster, 2014.
Bresnick et al., "Visual function abnormalities in macular heterotopia caused by proliferative diabetic retinopathy," American Journal of Ophthalmology, 1981, 92(1):85-102.
Burns et al., "Direct measurement of human-cone-photoreceptor alignment," Journal of the Optical Society of America A, 1995, 12(10):2329-2338.
Burns et al., "Variations in photoreceptor directionality across the central retina," J. Opt. Soc. Am. A, 1997, 14(9):2033-2040.
Choi et al., "Evidence for transient forces/strains at the optic nerve head in myopia: repeated measurements of the Stiles-Crawford effect of the first kind (SCE-I) over time," Ophthalmic Physiol Opt, 2004, 24(3):194-206.
Choi et al., "The relationship between the Stiles-Crawford effect of the first kind (SCE-I) and myopia," Ophthalmic Physiol Opt, 2003, 23(5):465-472.
Delint et al., "Local photoreceptor alignment measured with a scanning laser ophthalmoscope," Vision research, 1997, 37(2)243-248.
Delint et al., "Photoreceptor function in unilateral amblyopia," Vision Res., 1998, 38(4):613-617.
Eckmiller, "Defective cone photoreceptor cytoskeleton, alignment, feedback, and energetics can lead to energy depletion in macular degeneration," Progress in retinal and eye research, 2004, 23(5):495-522.
Enoch et al., "An analysis of retinal receptor orientation," Invest. Ophtalmol., 1971, pp. 959-970.
Enoch et al., "An analysis of retinal receptor orientation. 3. Results of initial psychophysical tests," Investigative ophthalmology, 1972, 11(9):765-782.
Enoch, "Amblyopia and the Stiles-Crawford effect," American journal of optometry and archives of American Academy of Optometry 34, 1957, 298-309.
Enoch, "Amblyopia, eccentric fixation and the Stiles-Crawford effect," American journal of optometry and archives of American Academy of Optometry 47, 1970, 482-484.
Enoch, "Further studies on the relationship between amblyopia and the Stiles-Crawford effect," American journal of optometry and archives of American Academy of Optometry, 1959, 36(3):111-128.
Enoch, "Optical Properties of the Retinal Receptors," J. Opt. Soc. Am., 1963, 53(1):71-85.
Gorrand et al., "A reflectometric technique for assessing photoreceptor alignment," Vision research, 1995, 35(7):999-1010.
He et al., "Comparison of cone directionality determined by psychophysical and reflectometric techniques," Journal of the Optical Society of America. A, Optics, image science, and vision, 1999, 16(10):2363-2369.
Headington et al., "Single Cell, In vivo Imaging of the Chick Retina with Adaptive Optics," Current Eye Research, 2011, 36(10):947-957.
Kanis et al., "Foveal cone-photoreceptor integrity in aging macula disorder," Investigative Ophthalmology & Visual Science, 2008, 49(5):2077-2081.
Keunen et al., "Stiles-Crawford effect and color matching in Stargardt's disease," American Journal of Ophthalmology, 1991, 112(2):216-217.
Lakshminarayanan et al., "Photoreceptor orientation and alignment in nasal fundus ectasia," Optom Vis Sci, 1997, 74(12):1011-1018.
Lardenoye et al., "Photoreceptor function in eyes with macular edema," Invest Ophthalmol Vis Sci, 2000, 41(12):4048-4053.
MacLeod, "Directionally selective light adaptation: A visual consequence of receptor disarray?," Vision Research, 1974, 14(6):369-378.
Marcos et al., "Cone spacing and waveguide properties from cone directionality measurements," Journal of the Optical Society of America. A, Optics, image science, and vision, 1999, 16(5):995-1004.
Marshall et al., "Amblyopia, eccentric fixation and the Stiles-Crawford effect," American journal of optometry and archives of American Academy of Optometry 47, 1970, 484-486.
Rativa et al., "Analysis of individual cone-photoreceptor directionality using scanning laser ophtalmoscopy," Biomed. Opt. Express, 2011, 2(6):1423-1431.
Roorda et al., "Optical fiber properties of individual human cones," J Vis, 2002, 2(5):404-412.
Smith et al., "Color matching and Stiles-Crawford effect in central serous choroidopathy," Mod Probl Ophthalmol, 1978, 19:284-295.
Smith et al., "Color matching and the Stiles-Crawford effect in observers with early age-related macular changes," Journal of the Optical Society of America a-Optics Image Science and Vision, 1988, 5(12):2113-2121.
Stiles et al., "The Luminous Efficiency of Rays Entering the Eye Pupil at Different Points," Proceedings of the Royal Society of London. Series B, Containing Papers of a Biological Character, 1933, 112(778):428-450.
van Blockland, "Directionality and aligment of the foveal photoreceptors assessed with light scattered from the human fundus in vivo," Vision research, 1986, 26(3):495-500.
Westheimer, "Directional sensitivity of the retina: 75 years of Stiles-Crawford effect," Proc Biol Sci, 2008, 275(1653):2777-2786.
International Search Report and Written Opinion for Application No. PCT/US2016/029717 dated Jul. 25, 2016 (9 pages).

RAPID MEASUREMENT OF INDIVIDUAL CONE PHOTORECEPTOR POINTING FOR EVALUATION OF EYE HEALTH USING FOCUS DIVERSITY

CROSS-REFERENCE TO RELATED APPLICATION(S)

This application is a U.S. national stage entry of International Patent Application No. PCT/US2016/029717, filed on Apr. 28, 2016, which claims the benefit of U.S. Provisional Patent Application No. 62/154,490, filed on Apr. 29, 2015, the entire contents of each of which are fully incorporated herein by reference.

BACKGROUND

The present invention relates to systems and methods for evaluating ocular and potentially systemic health based on the pointing direction of cone photoreceptors.

Figure 1A:
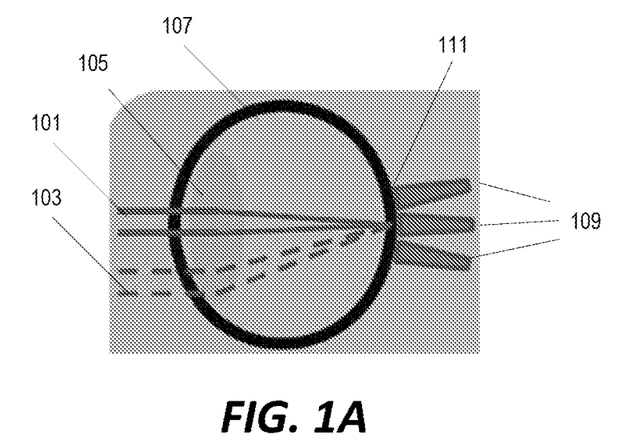
FIG. 1A is a cross-sectional schematic view of light being projected into an eye.
Figure 1B:
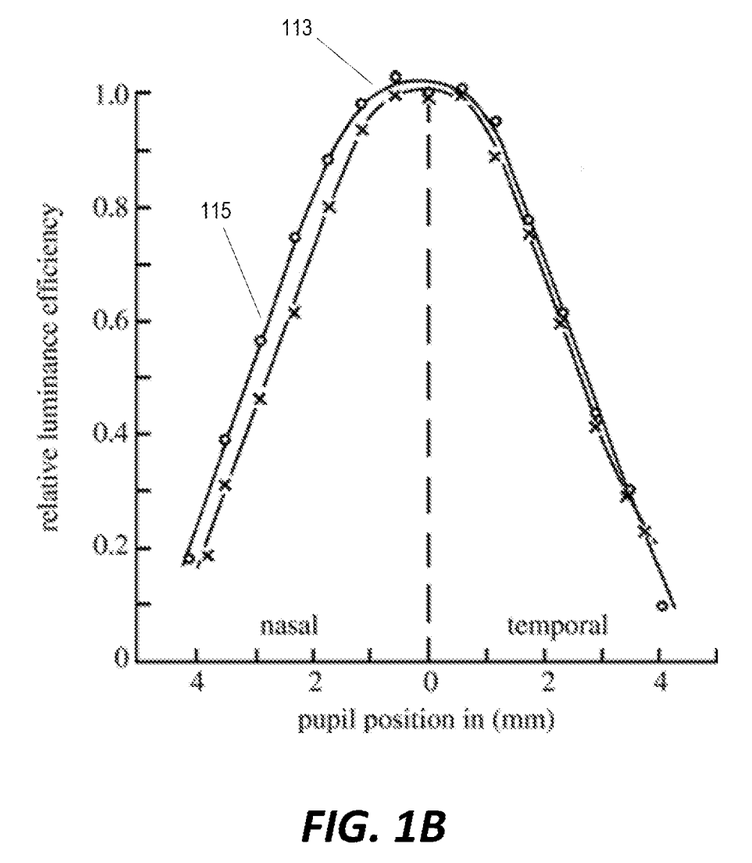
FIG. 1B is a graph of the SCE-I effect on the eye of FIG. 1A.

The Stiles-Crawford Effect of the First Kind (SCE-I) describes how rays of light entering near the center of the eye's pupil appear brighter to an observer than rays incident near the periphery. FIG. 1A illustrates this effect by showing a first centered ray of light 101 and a second off-center ray 103 of light 103 entering the pupil 105 of the eye 107 and reaching photoreceptor cones 109 at the retina 111. The graph of FIG. 1B shows perceived intensity of the light (y-axis) as a function of displacement from center of the pupil (x-axis). As shown in FIG. 1B, the perceived intensity of the first light ray 101 is much higher (point 113) than the perceived intensity of the second light ray 103 (point 115 in the graph). This effect is due to the waveguide properties of the cone photoreceptors, and it has been demonstrated that various eye conditions such as amblyopia, retinal detachment and retinal degeneration have an altered SCE-I function.

Photoreceptor tilt can be measured based on the SCE-I. Prior measurement of the photoreceptor tilt has typically been performed psychophysically as a subjective comparison of the perceived intensity of a flickering stimulus relative to a static background. The stimulus would be moved across the subject's pupil to measure the luminance efficiency as a function of pupil eccentricity. This subjective method required lengthy experimental sessions and a high degree of concentration and cooperation from test subjects, making it impractical to be a routine clinical measurement technique.

Other, more time efficient techniques analyze the intensity distribution of reflected light at the pupil plane. The distribution of light reflected back from the retina, illuminated from a small source, is measured in the plane of the eye's pupil. The distribution of the reflected light returning from the retina presents a peaked profile. These pupil plane reflectometric techniques similarly provide an estimate of the pupil location towards which the photoreceptors are pointing; however the directionality is greater (higher rho values) than that measured psychophysically. Both of these approaches measure the properties of an ensemble of cones and are incapable of measuring the directionality of individual cones.

SUMMARY

Various embodiments of the invention provide a rapid technique for measuring directionality of single cone photoreceptors. In a healthy eye, all of the cone photoreceptors generally point towards the center of the pupil or with a slight nasal bias, while in diseased eyes, there is more disarray. Measurement of the disarray may be an early indicator of retinal and/or systemic disease including, for example, age-related macular degeneration (AMD). In some medical conditions, cone disarray may be an observable precursor to cell death (i.e., reductions in photoreceptor density). When cone disarray is detected using the methods and techniques described in this disclosure, drug therapies and other treatment types might be prescribed to preserve photoreceptor function. Earlier diagnosis leads to earlier treatment and potentially improved treatment outcomes.

Some embodiments use adaptive optics (AO) to overcome the aberrations of the eye allowing for resolution at the level of individual cone photoreceptors. However, other embodiments are able to image individual cone photoreceptors without adaptive optics using imaging devices such as, for example, a non-AO fundus camera or a scanning laser ophthalmoscope (SLO).

Individual cones can be imaged and their apparent location measured relative to their neighbors. Each of these cones can be regarded as individual optical fibers that reflect light in a well-defined beam towards the center of the eyes pupil. An imaging system captures images of the retina at one or more focus positions. This can be accomplished in rapid succession, but the speed of acquisition does not affect the resulting measurement. By comparing the apparent lateral positions of the cones with changing focal position the directionality or pointing of individual cones can be determined.

Whereas existing techniques are subjective in nature and can take around 40 minutes to complete, the techniques described herein provide objective analysis and multiple images at various focal positions can be acquired in just a few seconds. Capturing multiple measurements at a number of retinal locations provides a move complete sample for diagnosis of potential disarray. These techniques and systems can be developed as a stand-alone camera system or may be incorporated into other optical imaging systems including, but not necessarily limited to, fundus cameras, scanning laser ophthalmoscopes, or an OCT imaging device.

In one embodiment, the invention provides a method of measuring angular direction of individual photoreceptors in an eye. A light source is projected through the pupil of the eye onto the retina. An image of the light reflected back from the plurality of photoreceptors is captured at a first focal depth and then at a second focal depth, where the first focal depth is different than the second focal depth. At least one individual photoreceptor is identified in both images and a lateral difference of the position of the identified photoreceptor is measured. The angular direction of the photoreceptor is then calculated based on the measured lateral difference. In some embodiments, the focal depth is adjusted using an adaptive optics (AO) mechanism (e.g., a lens or a mirror) while, in other embodiments, the focal depths is adjusted using a non-AO mechanism (e.g., a linearly moveable lens).

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

As discussed above, FIGS. 1A and 1B illustrate a mechanism for observing tilt of a photoreceptor using the Stiles-Crawford Effect of the first kind (SCE-I). Using an imaging system of sufficient quality (i.e., resolution) to image the location of single cones relative to their neighbors, it is possible to measure the tilt of individual cone photoreceptors by acquiring images while displacing the entrance pupil over the subject's pupil. By comparing the intensities of the individual cones imaged as the entrance pupil is displaced, one can compute the pointing direction for each imaged cone.

It has been demonstrated that various eye conditions and diseases have an altered SCE-I function. In myopic eyes, a systematic nasal shift in the peak position of the SCE-I function in the nasal retina with an increase in myopia has been reported (see, e.g., Choi, S. S., Garner, L. F., & Enoch, J. M. (2003). The relationship between the Stiles-Crawford effect of the first kind (SCE-I) and myopia. *Ophthalmic and Physiological Optics*, 23 (5), 465-472, and Choi, S. S., Enoch, J. M., & Kono, M. (2004). Evidence for transient forces/strains at the optic nerve head in myopia: repeated measurements of the Stiles-Crawford effect of the first kind (SCE-I) over time. *Ophthalmic Physiol Opt*, 24 (3), 194-206). Changes in the SCE-I function have also been found in a number of ocular diseases such as central serous chorioretinopathy (see, e.g., Smith, V. C., Pokorny, J., & Diddie, K. R. (1978). Color matching and Stiles-Crawford effect in central serous choroidopathy. *Mod Probl Ophthalmol*, 19, 284-295), retinitis pigmentosa (see, e.g., Birch, D. G., Sandberg, M. A., & Berson, E. L. (1982). The Stiles-Crawford effect in retinitis pigmentosa. *Invest Ophthalmol Vis Sci*, 22 (2), 157-164), age-related macular degeneration (see, e.g., Kanis, M. J., Wisse, R. P. L., Berendschot, T. T. J. M., van de Kraats, J., & van Norren, D. (2008). Foveal cone-photoreceptor integrity in aging macula disorder. *Investigative Ophthalmology & Visual Science*, 49 (5), 2077-2081), and a range of other retinal conditions (see, e.g., Smith, V. C., Pokorny, J., & Diddie, K. R. (1988). Color matching and the Stiles-Crawford effect in observers with early age-related macular changes. *Journal of the Optical Society of America a-Optics Image Science and Vision*, 5 (12), 2113-2121; Bedell, H. E., Enoch, J. M., & Fitzgerald, C. R. (1981). Photoreceptor orientation. A graded disturbance bordering a region of choroidal atrophy. *Arch Ophthalmol*, 99 (10), 1841-1844; Keunen, J. E., Smith, V. C., Pokorny, J., & Mets, M. B. (1991). Stiles-Crawford effect and color matching in Stargardt's disease. *American Journal of Ophthalmology*, 112 (2), 216-217; Lakshminarayanan, V., Bailey, J. E., & Enoch, J. M. (1997). Photoreceptor orientation and alignment in nasal fundus ectasia. *Optom Vis Sci*, 74 (12), 1011-1018; and Lardenoye, C. W., Probst, K., DeLint, P. J., & Rothova, A. (2000). Photoreceptor function in eyes with macular edema. *Invest Ophthalmol Vis Sci*, 41 (12), 4048-4053). Changes in SCE-I function have also been linked to diabetic retinopathy (see, e.g., Bresnick, G. H., Smith, V., & Pokorny, J. (1981). Visual function abnormalities in macular heterotopia caused by proliferative diabetic retinopathy. *American Journal of Ophthalmology*, 92 (1), 85-102). Because SCE-I has its origin at the retina, techniques that detect changes in photoreceptors could be used, for example, to diagnose and monitor patients with retinal diseases at a much earlier stage.

Figure 2:
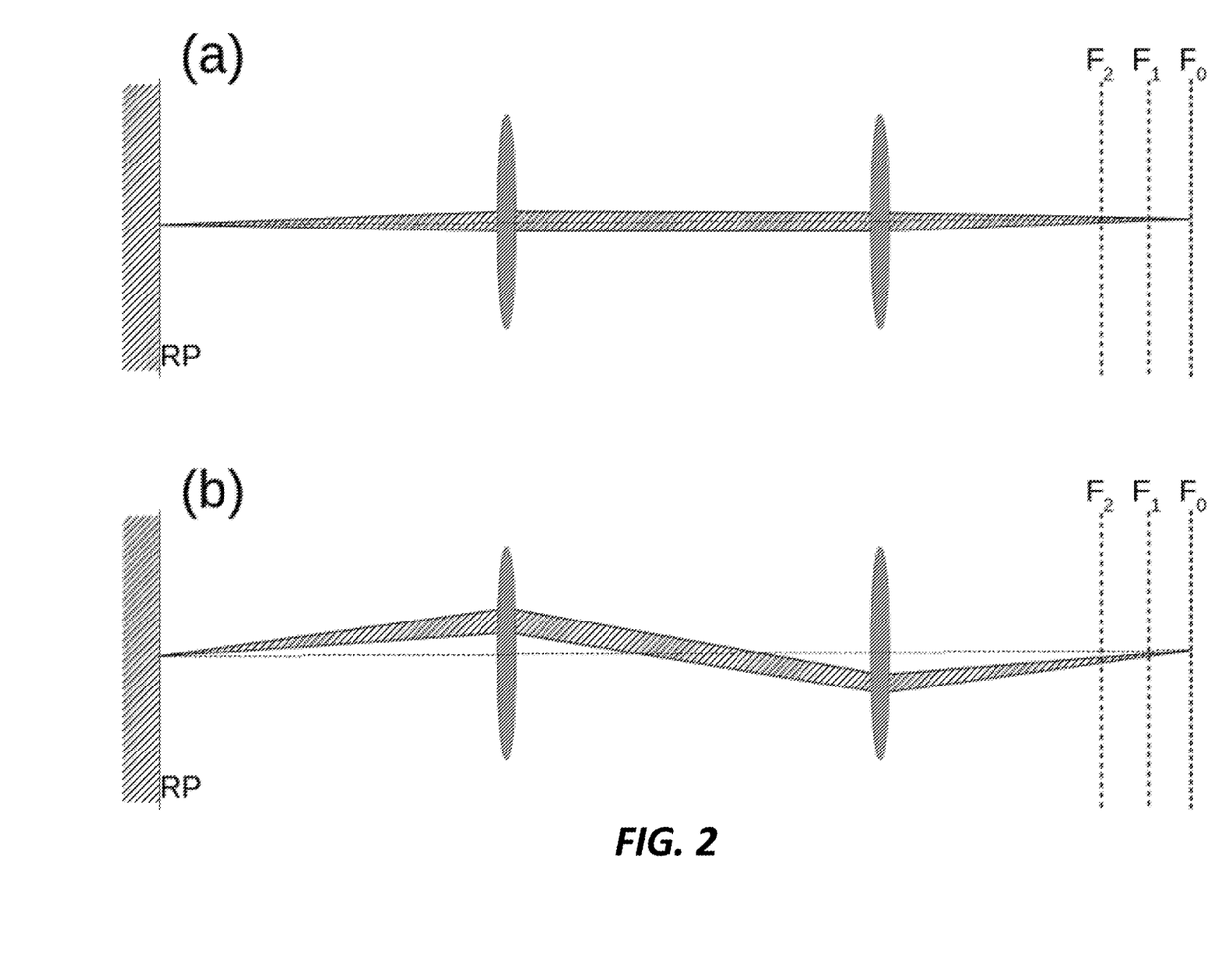
FIG. 2 is a graph of the effect of focus diversity for a centered cone photoreceptor and for an angled cone photoreceptor.

FIG. 2 illustrates an example of a technique, as implemented in some of the systems and methods of this disclosure, utilizing the principle of focus diversity to determine a pointing direction of a photoreceptor (for example, a cone photoreceptor) by comparing the lateral position of imaged cones as the focus of an imaging device is changed. Consider an imaging system designed such that points on the object plane (retinal plane RP) are conjugate to points in the nominal focal plane F0. When a camera sensor is placed in the F0 plane, point sources on RP will appear 'in focus' with the most compact PSFs. In FIG. 2, two cones are shown emitting narrow beams from the RP plane, one oriented along the optical axis and the other with a relative tilt. Both beams form compact images in the focal plane F0.

In graph (a) of FIG. 2, the narrow beam (shaded) is parallel with the overall optical axis and arrives at the focal plane still parallel with the optical axis. This is true for all RP points since the imaging system is designed to be jointly telecentric in the object and image spaces. If the camera were 'defocused' by moving it to another plane, say F1 or F2, the beam's image would become broader, but would not shift in lateral position. The situation is different when the narrow beam leaves RP in a tilted direction (e.g., due to photoreceptor disarray) as in the example of graph (b) of FIG. 2. The image is still formed at the same position in F0, but, in other defocused planes, the image is both broadened and shifted.

Figure 3A:
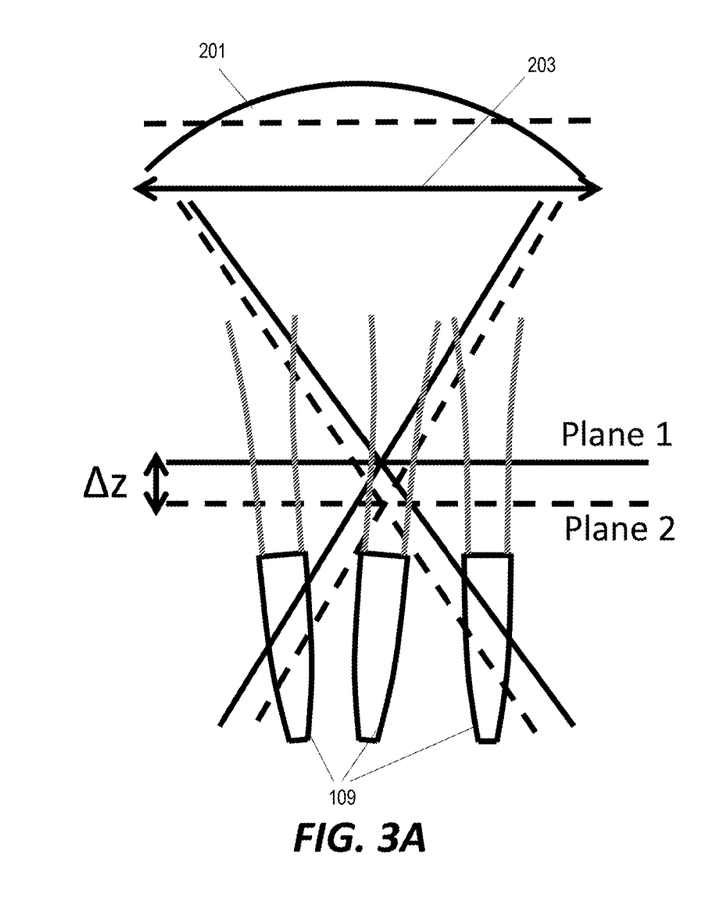
FIG. 3A is a cross-sectional schematic view of a method of a focal plane adjustment in an eye for measuring cone angle using focus diversity.
Figure 3B:
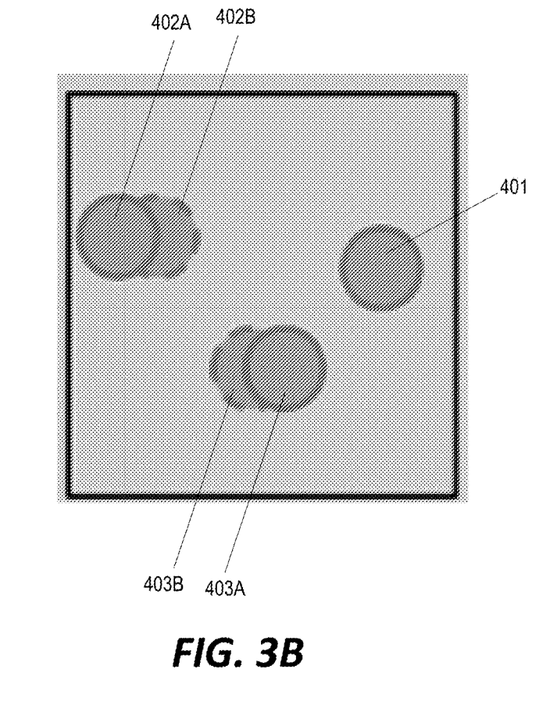
FIG. 3B is an overlaid view of the output of a camera system demonstrating lateral movement of reflected light from a cone photoreceptor.

FIGS. 3A and 3B provide a specific example of this effect on an eye and illustrate one example of a technique for monitoring and detecting this effect. As shown in FIG. 3A, a light source is projected into the pupil of a patient's eye and the light is reflected back by each of three individual cone photoreceptors 109. The focus of a camera imaging system is then adjusted to observe the reflected light at two different focal depths shown in FIG. 3A as Plane 1 and Plane 2. As shown in FIG. 3B, the first cone appears in the same location 401 in both the first focus position and in the second focus position. However, the position of the second cone appears to move laterally from location 402A in the first focal depth to location 402B in the second focal depth. Similarly, the position of the third cone appears to move from location 403A to location 403B.

As such, it can be concluded that the first cone is positioned at an angle that is substantially collinear with the imaging axis. However, the second and third cones are positioned at other angles relative to the imaging axis. The apparent lateral movement of the cones in the images acquired at different focal depths can be used to calculate an angle of each cone relative to the imaging axis.

FIG. 3A also illustrates one specific example of a mechanism for adjusting the focus of the imaging system using a deformable mirror 201 and a focusing lens 203 positioned between the deformable mirror and the cone photoreceptors 109. When the deformable mirror 201 is controllably deformed into a first condition (represented by the solid, curved line), the imaging system is focused at the first plane (Plane 1) as indicated by the intersection at Plane 1 of the solid lines extending from the deformable mirror 201. The deformable mirror 201 is then controllably deformed into a second condition (represented by the substantially straight dashed line) thereby focusing the imaging system at the second plane (Plane 2) as indicated by the intersection at Plane 2 of the dashed lines extending from the deformable mirror 201. As such, as illustrated in the example of FIG. 3A, the focus of the imaging system can be adjusted in some implementations using a deformable mirror such as in an adaptive optics (AO) system. However, as discussed in further detail below, in other implementations, the focus of the imaging system can be adjusted to capture images of the light reflected from the photoreceptors at multiple different focal depths using other types of AO and non-AO focusing mechanism.

Figure 4:
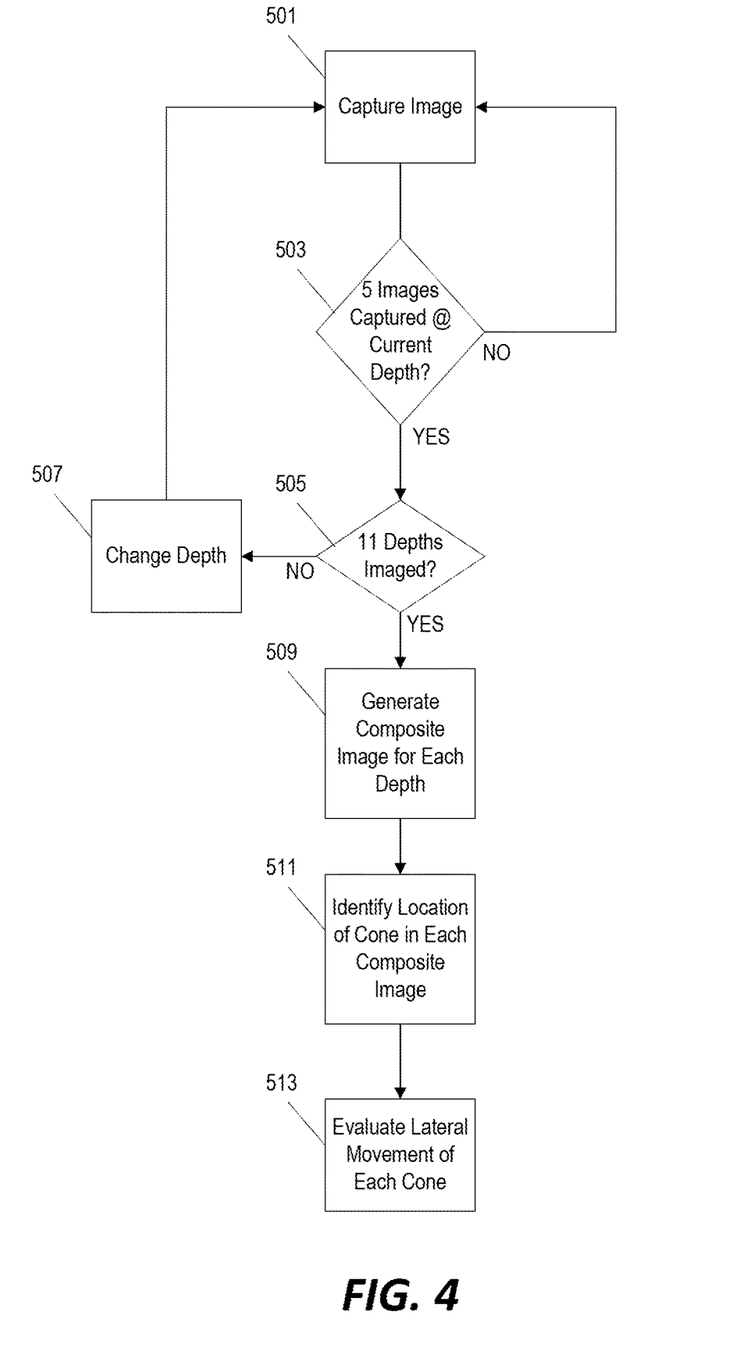
FIG. 4 is a flowchart of a method for measuring angle of individual cone photoreceptors using focus diversity.

FIG. 4 illustrates a specific example of the processing steps involved in determining the angle of each individual cone photoreceptor relative to an imaging axis. Retinal images are rapidly acquired at 11 focal positions over a physical depth range of ±40 μm in the subject's retina, with 5 retinal images being acquired at each position. An image is captured (step 501) and is repeated until five retinal images have been acquired at a given position (step 503). The imaging system then changes the focal depth (step 507) and repeats the image acquisition step (steps 501 and 503) until five images have been captured at each of 11 focal depth positions (step 505). It is noted that, although the example of FIG. 4 captures five images at each of 11 different focal positions, other implementations may capture more or fewer images at each position and may utilize more or fewer distinct focal positions.

The 55 images were then registered together (compensating for any shift, rotation and magnification changes between images). The 5 images acquired at the same depth were averaged to improve the signal-to-noise ratio and the contrast of the cones (step 509). The final stack consisted of 11 images, each of them corresponding to a different depth in the retina.

The cones on each image were then identified with an automated custom MATLAB® routine and the cones in each image were matched (step 511). A cone identified at one depth and a cone identified at another depth are considered to be the same cone if the distance between the two is smaller than a threshold distance, typically 3-4 pixels. If the distance was more than this threshold distance, they were not considered to be the same cone.

The coordinates of each identified cone were automatically measured on every image allowing measurement of the apparent relative lateral displacement of each cone as the depth is scanned (step 513). Since the axial distance $\delta F$ between two images and the lateral displacement of the cones on different images are known, the relative angle that the cones subtend with respect to the average pointing direction of the ensemble in the field of view (FOV) can be computed. The focus diversity data, however, only gives the relative pointing angle between the individual cones identified on the images. To obtain the overall pointing direction of the ensemble that are imaged, simultaneous pupil intensity images can also be acquired using the same light source (e.g., a 680 nm light source) with a camera conjugate with the pupil plane of the subject.

Figure 5:
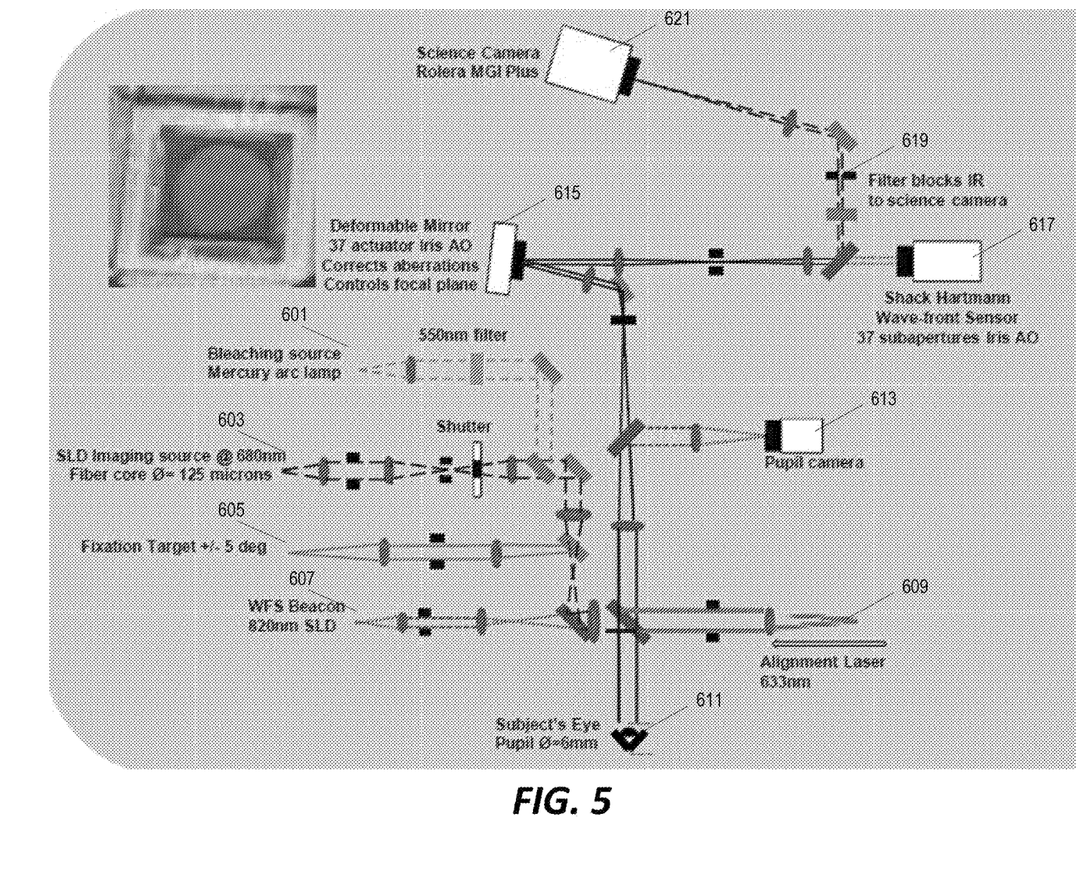
FIG. 5 is a schematic diagram of a system for measuring angle of individual cone photoreceptors using the method of FIG. 4.

FIG. 5 illustrates a specific example of a system configured to perform the method of FIG. 4. An AO Flood Illuminated Retinal Camera is used to acquire the retinal images. A bleaching source mercury arc lamp 601, an SLD imaging source 603, a fixation target 605, a WFS beacon 607, an alignment laser 609, and various associated optics are configured to project light into the subject's eye pupil 611 to illuminate the cone photoreceptors. A pupil camera 613 monitors the pupil of the subject and a deformable mirror 615 is used to control the conjugate plane by adding a known and controlled amount of defocus to the wavefront. A Shack Hartmann Wavefront Sensor 617 and a Science Camera 621 are used to capture images of the reflected light from the cones. A filter 619 blocks IR before the light reaches the Science Camera 621. A series of images captured by the Science Camera 621 are stored for later analysis. Each image recorded is the image of the irradiance at the conjugate plane of the sensor in the retina (e.g., Plane 1 and Plane 2 as illustrated in FIG. 3A).

Adaptive optics (AO) systems—such as, for example, the RTX1 retinal camera by Imagine Eyes)—typically have a field of view ranging from 1-4 degrees. However, with proper registration, multiple images are combined to apply the focus diversity methods described above to a much wider field of view. Furthermore, other imaging devices that do not utilize adaptive optics—such as, for example, a scanning laser ophthalmoscope—can be used to image individual cones over a field of view of 5.5 degrees. The systems and methods described above can utilize other imaging devices and techniques to apply the focus diversity technique without necessarily including adaptive optics. In some such systems, the focus of the imaging system can be adjusted by mechanically moving a lens linearly along an optical pathway between the camera/imaging device and the eye of the imaging subject. In other implementations, the focus of the imaging system can be adjusted by other mechanisms including, for example, electro-optic lenses, water-filled lenses, and liquid crystal devices.

The focus diversity method allows for a very rapid measurement of the pointing direction of individual cones in the field of view of a camera. The computation cost and algorithmic complexity is not significantly increased and the accuracy of the method is comparable to previous techniques. Results obtained on a cone-per-cone basis are in good agreement with measurements made on the same subjects with other photoreceptor tilt measuring techniques.

Thus, the invention provides, among other things, a non-invasive method of measuring angle positioning of individual cone photoreceptors using focus diversity. Various features and advantages of the invention are set forth in the following claims.

What is claimed is:

1. A method of measuring angular direction of individual photoreceptors in an eye, the method comprising:
projecting a light from a light source through a pupil of the eye onto a retina of the eye;
capturing an image of light reflected back from a plurality of photoreceptors at a first focal depth;
capturing an image of light reflected back from the plurality of photoreceptors at a second focal depth, the second focal depth being different than the first focal depth;

identifying at least one individual photoreceptor in the image captured at the first focal depth and in the image captured at the second focal depth;

measuring a lateral difference of a position of the identified at least one individual photoreceptor between the image captured at the first focal depth and the image captured at the second focal depth; and calculating an angular direction of the at least one individual photoreceptor based on the measured lateral difference.

2. The method of claim 1, wherein capturing an image of light reflected back from the plurality of photoreceptors includes capturing an image by an imaging device capable of imaging individual photoreceptors.

3. The method of claim 2, wherein the imaging device is one selected from a group consisting of an optical-coherence tomography system, a scanning laser ophthalmoscope, and a fundus camera.

4. The method of claim 1, further comprising changing the focal depth of an imaging device from the first focal depth to the second focal depth after capturing an image at the first focal depth and before capturing an image at the second focal depth.

5. The method of claim 4, wherein changing the focal depth of the imaging device includes operating a controllably deformable mirror to change the focal depth of the imaging device from the first focal depth to the second focal depth.

6. The method of claim 4, wherein changing the focal depth of the imaging device includes controllably operating a non-adaptive optics defocus mechanism selected from a group consisting of a linearly-movable lens, an electro-optic lens, a fluid-filled lens, and a liquid crystal device.

7. The method of claim 4, further comprising:
capturing a first plurality of images at the first focal depth;
generating a first composite image from the first plurality of images captured at the first focal depth;
capturing a second plurality of images at the second focal depth; and
generating a second composite image from the second plurality of images captured at the second focal depth,
wherein measuring the lateral difference of the position of the identified at least one individual photoreceptor includes identifying the lateral difference of the position of the identified at least one individual photoreceptor in the first composite image relative to the position of the identified at least one individual photoreceptor in the second composite image.

8. The method of claim 1, further comprising capturing an image of light reflected back from a plurality of photoreceptors at more than two focal depths.

9. The method of claim 1, further comprising:
identifying a plurality of individual photoreceptors in the image captured at the first focal depth;
identifying each photoreceptor of the plurality of photoreceptors in the image captured at the second focal depth; and
measuring a lateral difference of a position of each photoreceptor of the plurality of individual photoreceptors between the image captured at the first focal depth and the image captured at the second focal depth.

10. The method of claim 1, wherein identifying the at least one individual photoreceptor in the image captured at the first focal depth and in the image captured at the second focal depth includes performing a registration between the image captured at the first focal depth and the image captured at the second focal depth to identify the same individual photoreceptor in both the image captured at the first focal depth and the image captured at the second focal depth.

11. A system for detecting and measuring photoreceptor disarray, the system comprising:
a source positionable to project light through a pupil of an eye onto a retina of the eye;
an adjustable-focus imaging system configured to capture an image of light reflected back from a plurality of photoreceptors of the eye at a plurality of different focal depths; and
an image processing system configured to
identify an individual photoreceptor in an image captured by the adjustable-focus imaging system at a first focal depth of the plurality of focal depths,
identify the same individual photoreceptor in an image captured by the adjustable-focus imaging system at a second focal depth of the plurality of focal depths, and
measure a first lateral difference between a position of the individual photoreceptor in the image captured at the first focal depth and a position of the individual photoreceptor in the image captured at the second focal depth.

12. The system of claim 11, wherein the image processing system further configured to
identify a second individual photoreceptor in the image captured at the first focal depth,
identify the same second individual photoreceptor in the image captured at the second focal depth,
measure a second lateral difference between a position of the second individual photoreceptor in the image captured at the first focal depth and the position of the second individual photoreceptor in the image captured at the second focal depth, and
evaluating photoreceptor disarray based on a comparison of the first lateral difference and the second lateral difference.

13. The system of claim 11, wherein the adjustable-focus imaging system includes at least one imaging device selected from a group consisting of an optical-coherence tomography system, a scanning laser ophthalmoscope, and a fundus camera.

14. The system of claim 11, wherein the adjustable-focus imaging system includes an adaptive optics component selected from a group consisting of a controllably deformable mirror and a controllably deformable lens, and wherein the adjustable-focus imaging system captures images at the plurality of different focal depths by operating the adaptive optics component to change the focal depth of the imaging system from the first focal depth to the second focal depth.

15. The system of claim 11, wherein the adjustable-focus imaging system includes a lens, and wherein the adjustable-focus imaging system captures images at the plurality of different focal depths by controllably adjusting a position of the lens in a linear direction and capturing at least one image at each of a plurality of positions along the linear direction.

16. The system of claim 11, wherein the image processing system is further configured to
generate a first composite image from a first plurality of images captured by the adjustable-focus imaging system at the first focal depth, and
generate a second composite image from a second plurality of images captured by the adjustable-focus imaging system at the second focal depth,
wherein the image processing system is configured to measure the lateral difference of the position of the individual photoreceptor by identifying the lateral difference between a position of the individual photoreceptor in the first composite image and a position of the same individual photoreceptor in the second composite image.

17. The system of claim 11, wherein the image processing system is further configured to measure a plurality of lateral differences in a position of the individual photoreceptor from a plurality of images captured by the adjustable-focus imaging system at more than two focal depths.

18. The system of claim 11, wherein the image processing system if further configured to
- identify a plurality of individual photoreceptors in the image captured at the first focal depth;
- identify each photoreceptor of the plurality of photoreceptors in the image captured at the second focal depth; and
- measure a lateral difference of a position of each photoreceptor of the plurality of individual photoreceptors between the image captured at the first focal depth and the image captured at the second focal depth.

19. The system of claim 11, wherein the image processing system is configured to identify the individual photoreceptor in the image captured at the first focal depth and in the image captured at the second focal depth by performing a registration between the image captured at the first focal depth and the image captured at the second focal depth to identify the same individual photoreceptor in both the image captured at the first focal depth and the image captured at the second focal depth.

* * * * *

UNITED STATES PATENT AND TRADEMARK OFFICE
CERTIFICATE OF CORRECTION

Page 1 of 1

PATENT NO. : 10,231,618 B2
APPLICATION NO. : 15/570328
DATED : March 19, 2019
INVENTOR(S) : Nathan Doble et al.

It is certified that error appears in the above-identified patent and that said Letters Patent is hereby corrected as shown below:

In the Specification

Column 1, Line 16, please insert the following paragraph:
-- STATEMENT OF GOVERNMENT INTEREST
This invention was made with government support under grant number EY020901 awarded by the National Institutes of Health. The government has certain rights in the invention. --

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*